United States Patent [19]

Burch

[11] 3,995,324
[45] Dec. 7, 1976

[54] ACTUATOR DEVICE FOR ARTIFICIAL LEG

[75] Inventor: John L. Burch, Decatur, Ala.

[73] Assignee: The United States of America as represented by the Administrator of the National Aeronautics and Space Administration, Washington, D.C.

[22] Filed: Sept. 12, 1975

[21] Appl. No.: 612,965

[52] U.S. Cl. .................................... 3/1.2; 3/14
[51] Int. Cl.² ...................... A61F 1/08; A61F 1/00
[58] Field of Search ................ 3/1, 1.2, 2, 14, 15; 128/80 G

[56] References Cited
UNITED STATES PATENTS

| 3,553,738 | 1/1971 | Liberson | 128/80 G X |
| 3,663,967 | 5/1972 | Vermillion | 3/15 |

FOREIGN PATENTS OR APPLICATIONS

| 1,360,260 | 3/1964 | France | 3/15 |
| 1,236,818 | 6/1971 | United Kingdom | 3/14 |

Primary Examiner—Ronald L. Frinks
Attorney, Agent, or Firm—L. D. Wofford, Jr.; Gary F. Grafel; John R. Manning

[57] ABSTRACT

An actuator device is provided for moving an artificial leg of a person having a prosthesis replacing an entire leg and hip joint. The device includes a first articulated hip joint assembly carried by the natural leg and a second articulated hip joint assembly carried by the prosthesis whereby energy from the movement of the natural leg is transferred by a compressible fluid from the first hip joint assembly to the second hip joint assembly for moving the artificial leg.

12 Claims, 8 Drawing Figures

ACTUATOR DEVICE FOR ARTIFICIAL LEG

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

The disarticulation of a hip involves a replacement of an entire leg including the hip joint with a prosthesis designed to provide a portable, patient-controlled, stable platform on which the patient can rest his weight during the prosthesis weight bearing phase of the stride. In general, the prosthesis device primarily uses passive components having two major sections; a trunk socket in which the body portion of the replaced leg is received, and an artificial leg section including a thigh section, a lower leg section, and a foot section. Simple hinges join the sections at an artificial hip joint and the knee. Optimum performance is obtained through the proper alignment of the "prosthesis" section. Once the prosthesis is properly aligned and after a small amount of training, a patient can regain the ability to walk, but normally the patient's gait is badly distorted.

The distortion is caused primarily by the maneuvers through which the patient must go to lift the prosthetic leg and swing it forward to take the next step. The normal leg during its normal swing is flexed at both the hip and knee thus providing adequate clearance between the foot and the ground. Unfortunately, this is not the case with the artificial leg which is at its maximum length as the foot passes closest to the ground leaving no clearance since both the natural leg and the artificial leg are the same length. To obtain clearance, the patient elevates his hip on the prosthesis side and swings his prosthesis or artificial leg slightly to the side when bringing it forward or the patient vaults by raising on the toe of the normal foot in order to obtain clearance of the artificial leg. Obviously, the net result is a distorted gait.

The present invention provides a needed actuator device that can be attached to the prosthesis to store energy during one phase of the stride, and release this energy during another phase to pivot the artificial hip joint much as the natural hip joint flexes so as to eliminate a considerable amount of the gait distortion while also providing a faster cadence than might otherwise be possible. The device must be reliable and durable, and must be lightweight. The device must not interfere with the prosthesis assuming an extreme position such as sitting, but must move the thigh section forward rotating the thigh section approximately 20° about the hip pivot axis as the prosthetic foot leaves the ground. The amount of forward motion imparted to the thigh section must be closely controlled as too much motion will prevent the proper prosthesis alignment needed for the next step, and too little motion does not solve the gait distortion problem.

SUMMARY OF THE INVENTION

An actuator device is provided for moving an artificial leg of a person having a prosthesis replacing an entire leg and hip joint including a trunk socket carried about the person's waist for receiving the trunk portion of the removed leg and an artificial leg connected to said trunk socket by a pivotable hip joint. The artificial leg comprises an artificial thigh section, an artificial lower leg section, and an artificial foot section connected together by pivotable joints.

The actuator device comprises a first articulated hip joint assembly carried adjacent a natural leg of the person's body which includes a housing, a flexible bladder means carried within the housing containing a fluid, and compressing means carried with the housing connected to the natural leg for compressing the bladder means in response to the walking movement of the natural leg.

A second articulated hip joint assembly is carried by the trunk socket of the prosthesis and includes a housing, a flexible bladder means carried within said housing containing a fluid, and bladder engaging means carried within the housing connected to the artificial leg for moving the artificial leg in response to the bladder means being expanded. Conduit means interconnects the bladder means of the first and second hip joint assemblies.

Thus, movement of the natural leg causes the compressing means to compress the bladder means and fluid therein of the first hip joint assembly forcing the fluid through the conduit means into the bladder means of the second hip joint assembly to expand the bladder means to engage and move the bladder engaging means causing the artificial leg connected thereto to move in a natural walking motion.

Accordingly, an important object of the present invention is to provide a device for transferring the energy from the walking movement of a person's natural leg to supply the energy to move the artificial leg.

Another important object of the present invention is to provide an actuator device for moving an artificial leg so as to eliminate the distorted gait normally associated with the user of an artificial leg.

Another important object of the present invention is to provide an actuator device for utilizing the energy in a person's natural leg for supplying energy to move an artificial leg which is durable and lightweight and can be used as an attachment to an existing prosthesis or can be used as a built in device.

Another object of the present invention is to provide an actuator device for moving an artificial leg in a more natural and safer manner.

Still another object of the present invention is to provide an actuator device for moving an artificial leg which is simple in construction and is reliable, and which is readily affordable to all users of a hip and leg prosthesis.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

This invention relates to a device and a system for transferring energy from a natural limb for moving a corresponding artificial limb. While the energy transfer system and actuator device may have applications to many artificial limb members, particular problems have been associated with the use of an artificial leg to which this invention has particular advantages. Accordingly, the invention is illustrated in connection with a prosthesis for replacing a patient's entire leg.

Figure 1:
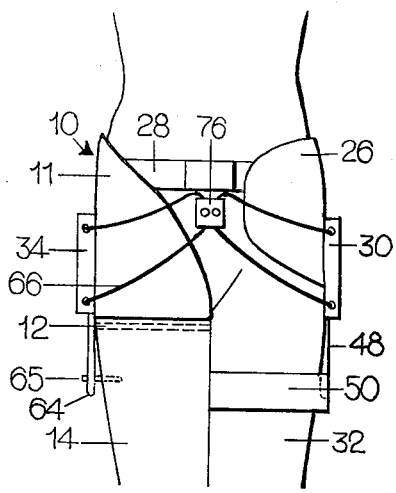
FIG. 1 is a front elevational view showing a person wearing a prosthesis actuator device for moving an artificial leg constructed in accordance with the present invention.
Figure 2:
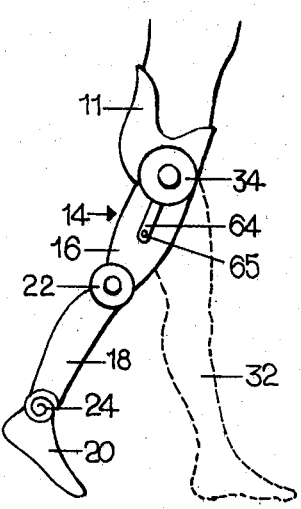
FIG. 2 is a side elevational view illustrating a prosthesis actuator device constructed in accordance with the present invention.
Figure 3:
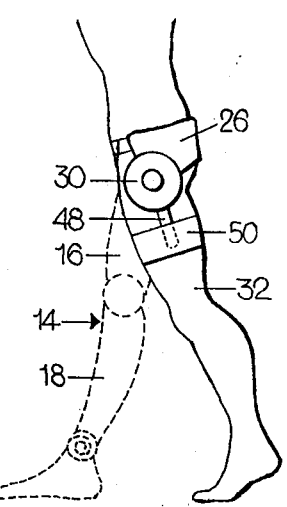
FIG. 3 is side elevational view illustrating the prosthesis actuator device constructed in accordance with the present invention attached to a person's natural leg.
Figure 4:
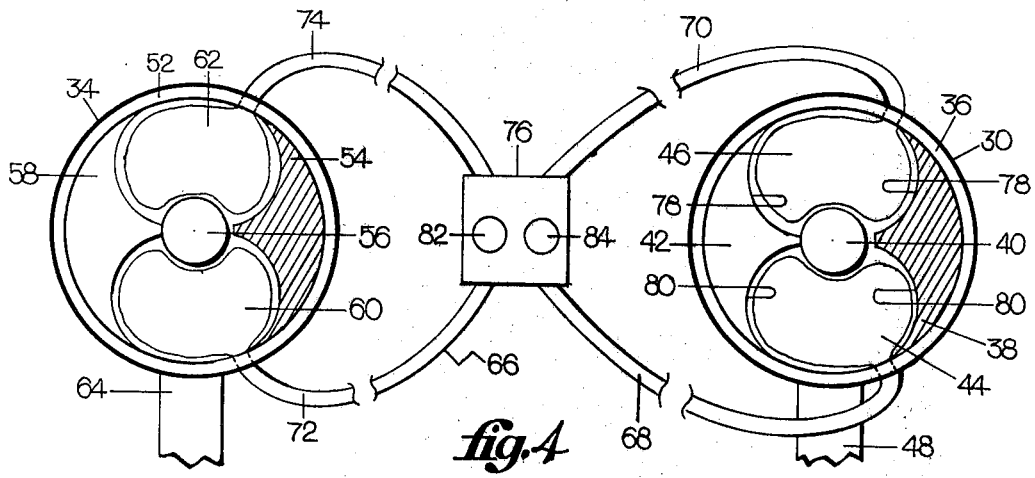
FIG. 4 is a schematic view illustrating a prosthesis actuator device constructed in accordance with the present invention for transferring energy from a person's natural leg to an artificial hip joint for moving an artificial leg.

Referring now to FIG. 1, a prosthesis, referenced generally at 10, is illustrated for replacing an entire leg and hip joint having a trunk socket portion 11 for receiving the trunk portion of the removed leg, a pivotable hip joint 12, and an artificial leg, referenced at 14, connected to the trunk socket by the pivotable joint 12 comprising an artificial thigh section 16, an artificial lower leg section 18, and an artificial foot section 20. The sections are connected together by conventional pivot joints 22 and 24.

The prosthesis 10 is carried about the patient's waist and has a side portion 26 which fits about the person's natural hip and a belt and buckle member 28 for fastening the prosthesis 10 about the person's waist.

The actuator device for moving the artificial leg 14 includes a first articulated hip joint assembly 30 carried by the side portion 26 adjacent a natural leg 32 of the person's body, and a second articulated hip joint assembly 34 carried by the trunk socket 11 of the prosthesis. The first hip joint assembly 30 includes a cylindrical housing 36, a fixed lobe member 38, a rotatable shaft 40 carried within the housing, and a movable lobe 42 carried on the shaft 40 for rotation therewith. A first flexible bladder 44 is carried in the housing on one side of the shaft 40 and a second flexible bladder 46 is carried on the opposite side of the shaft 40 providing flexible, resilient bladder means between the fixed and movable lobes 38 and 42, respectively. The first and second flexible bladders contain a suitable fluid for compression. The rotatable shaft 40 is connected to the natural leg 32 by a linkage arm 48 which is connected at one end to the shaft 40 and at the opposite end to the natural leg 32 by means of a suitable belt device 50. The fixed lobe 38, and the movable lobe 42 carried on the rotatable shaft 40 comprise compressing means for compressing the flexible bladders 44 and 46 in response to the walking movement of the natural leg.

The second articulated hip joint assembly 34 includes a housing 52, a fixed lobe member 54, a rotatable shaft 56 carried within the housing, and a movable lobe member 58 carried on the shaft 56. A first flexible bladder 60 and a second flexible bladder 62 carried in the housing on opposing sides of shaft 56 define flexible bladder means which contain a suitable compressible fluid. The flexible bladders may be constructed from any suitable resilient, flexible material having elastic, shape-retaining properties which can readily be expanded and compressed. The rotatable shaft 56 is connected to the thigh section 16 of the artificial leg 14 by means of a linkage arm 64 connected on one end to the rotatable shaft 56 and adjacent its opposite end to the thigh section at a pivotable connection 65 by any suitable means. As the linkage arm 64 moves backwards and forward, the artificial leg 14 pivots about the artificial pivotable hip joint 12 which may be any suitable hinge construction. The fixed lobe member 54 and the movable lobe member 58 carried on the rotatable shaft member 56 provide bladder engaging means connected to the artificial leg 14 for moving the artificial leg in response to the flexible bladders 60 and 62 expanded by the fluid compressed in the first hip joint assembly 30. Suitable conduit means 66 are provided for interconnecting the bladder means of the first and second hip joint assemblies 30 and 34, respectively. As the natural leg 32 moves forward, the shaft 40 and movable lobe 42, connected to the leg by arm 48, compress the fluid in the bladder 44 forcing the fluid through the conduit means 66 into the flexible bladder 62 carried in the hip joint assembly 34. As the fluid is pumped into the flexible bladder 62, the bladder expands engaging the movable lobe 58 to rotate the lobe counter-clockwise causing the linkage arm 64 and the artificial leg 14 connected thereto rotate accordingly.

Figure 5:
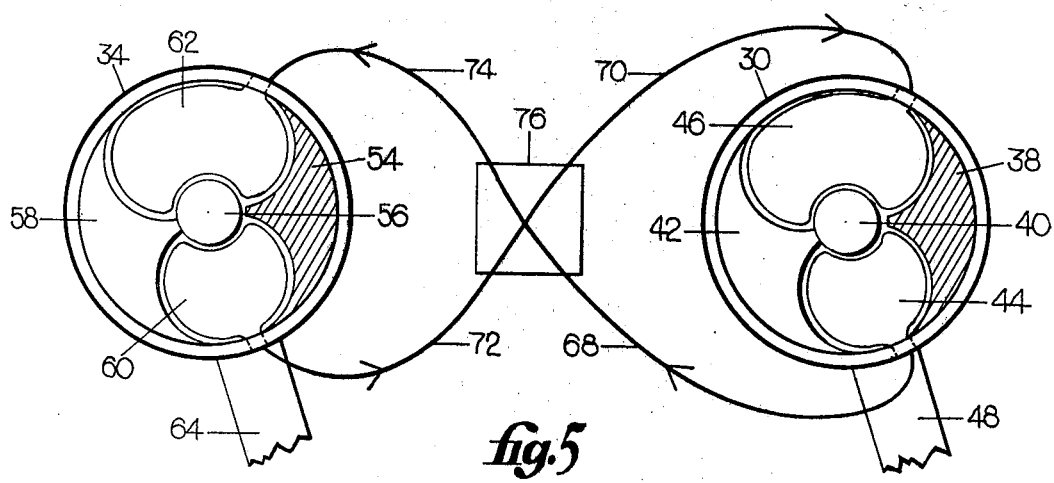
FIG. 5 is a schematic view illustrating the prosthesis actuator device in the position where the person's natural leg has moved forward and illustrating the walking time phase of the artificial leg.

The conduit means 66 may be any suitable flexible tubing or hose and includes a first hose section 68 connected to the bladder 44, a second hose section 70 connected to the bladder 46, a hose section 72 connected to the bladder 60, and a hose section 74 connected to the bladder 62. The opposite ends of the hose sections 68 through 74, are connected to a control valve 76. The control valve 76 controls the time phase relationship between the natural leg 32 and the artificial leg 14 in the following manner. During normal walking operations, the control valve 76 is placed in an out-of-phase mode for a delivering fluid from the bladder 44 to the bladder 62 by way of the hose sections 68 and 74. This causes the fluid in bladder 44 to be compressed as the natural leg 32 moves forward, as is best shown in FIG. 5, by the linkage arm 48 and the movable lobe 42 being moved by the leg in a counter-clockwise direction. The fluid is forced or pumped from the bladder 44 to the bladder 62 causing the bladder 62 to expand thereby moving the movable lobe member 58 in a counter-clockwise direction. Thus, the linkage arm 64 will rotate the artificial leg 14 forward at the appropriate time, that is when the person's weight is supported substantially entirely by the natural leg or approximately 180° out of time phase with the movement of the natural leg. To enhance the movement of the movable lobe 58 due to the expansion of the bladder 62, bladder 60 when compressed by such movement will have such compression relieved by flow of the fluid contained therein through the hose sections 72 and 70 to the bladder 46. Not only does this relieve the pressure in the bladder 60 making expansion of the bladder 62 easier, but pumping of the fluid into the bladder 46 adds to the counter-clockwise movement of the movable lobe 42 as the bladder 46 expands. Thus, when the natural leg 32 has been extended to its forwardmost position and the person's body has been moved over the natural leg into proper alignment therewith, the actuator device of the present invention will begin to bring the artificial leg 14 forward in the proper manner. At the time that the natural leg is at its forward position the artificial leg is at its backwardmost position and thus the two legs are 180° out-of-phase with respect to their timing.

As the natural leg 32 is pivoted rearwardly as the artificial leg swings forward, the linkage arm 48 moves clockwise, the movable lobe 42 rotates clockwise compressing the bladder 46, and the fluid therein is pumped to the bladder 60 by way of hose sections 70 and 72. The flexible bladder 60 increases in size or expands thus causing the movable lobe 58 to move clockwise moving the linkage arm 64 and the artificial leg 14 back into their original rearward position. Thus the lobe members and the flexible bladders in each of the hip joint assemblies 30 and 34 are brought back to their original positions and sizes in time for the natural leg to again move forwardly to begin the cycle over again.

The control valve means 76 may also be placed in an in-phase mode for delivering the compressed fluid from the bladder 44 to the bladder 60 by way of the hose sections 68 and 72. This provides for movement of the artificial leg and the natural leg in the same phase or time relationship such as for sitting and the like.

The fixed lobe member 38 and the movable lobe member 42 of the first hip joint assembly 30 oppose each othe and preferably are substantially quarter-circular lobe members having concave cut-out surfaces 78 and 80 spaced on opposing sides of the shaft 40 between which the bladders 46 and 44 are carried, respectively. The concave shape of the portions 78 and 80 provide a smooth surface between which the bladders are compressed so as not to puncture the bladder when pressure is applied thereto. The lobe members 58 and 54 of the second hip joint assembly 34 are shaped identical to the lobe members 38 and 42, and the bladders 62 and 60 are carried identically therebetween.

The control valve means 76 may be any suitable conventional valve for selectively connecting the hose sections 68 through 74 in the manner described above by selectively depressing either one of the control buttons 82 or 84.

Figures 6, 7, 8:
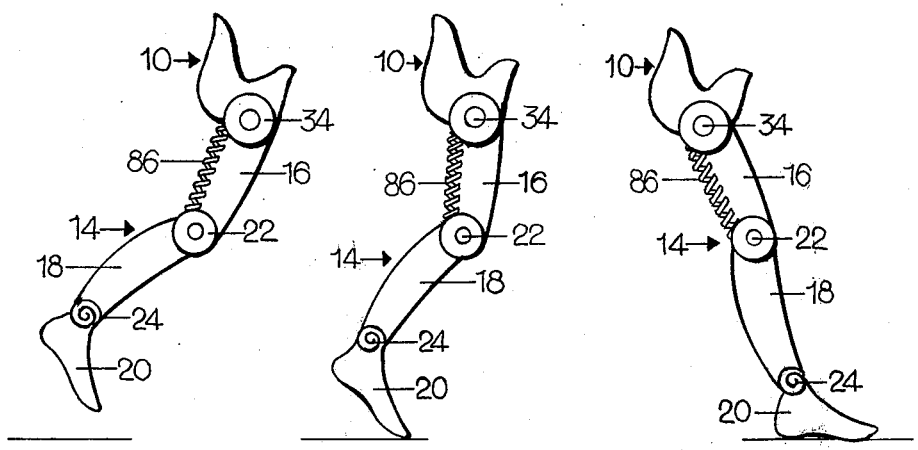
FIG. 6 is a schematic side view of the prosthesis illustrating an elastic cord for bending the artificial knee joint prior to forward motion of the artificial leg.
FIG. 7 is a schematic side view of the prosthesis of FIG. 6 illustrating the movement of the lower leg section of the artificial leg providing ground clearance as the artificial leg moves forward.
FIG. 8 is a schematic side view of the prosthesis illustrating the artificial leg in its forwardmost position.

Referring now to FIG. 6, the action of the artificial leg member 14 is illustrated under the motion of the articulated hip joint assembly 34. As the thigh section 16 has begun to rotate forward under the control of the hip joint assembly 34, an elastic cord member 86 is provided between the lower leg section 18 and the hip joint assembly 34 to lift the lower leg and foot flatly about the knee joint 22 to a slightly bent position. In FIG. 7, the thigh section 16 has rotated forward to a substantially vertical position and the knee joint 22 has rotated to a mechanical stop. The elastic cord 86 still has the foot lifted slightly so as to provide clearance of the foot section 20 above the ground. In FIG. 8, the thigh section 16 has reached its forward limit, and the lower leg 18 and foot section 20 have been carried by centrifugal force to their forward limit slightly ahead of the thigh section 16. The knee joint 22 is locked lightly in this position. The foot section 20 which is hinged slightly back of the center by the pivot joint 24 is rotated forward against a restraining spring contained within the pivot joint 24 by inertial forces. This causes the foot to straighten slightly and to, in effect reach for the ground thereby reducing shock and allowing the user to sense his footing. The joints 22 and 24 are conventional artificial knee and ankle joints used in a leg prosthesis.

As the person's body moves over the artificial leg 14 in a vertical position so as to place the artificial leg in a rearward position the thigh section 16 and the lower leg section 18 are in their same relative positions as shown in FIG. 6 thus the ankle joint 24 is rotated as necessary to keep the foot on the ground until the leg is slightly past the vertical position.

The housings 36 and 52 for the hip joint assemblies are shown schematically only but preferably would include a pair of opposed cylindrical plates between which the shafts 40 and 56 would be rotatably carried, as well as the flexible bladders, and which would enclose the housings on both sides.

Thus, an advantageous energy transfer system and actuator device for transferring the energy from a natural leg to an artificial leg is provided by the present invention. The advantageous construction provides a more natural, safe means for walking for people wearing artificial legs who have suffered a hip disarticulation which can be added on to an existing prosthesis. The add-on system is lightweight, reliable, durable and inexpensive. The add-on system does not require external power, precision parts or fluid seals and requires little or no maintenance. The advantageous lobe and bladder construction provide a positive displacement fluid type hip joint.

While a preferred embodiment of the invention has been described using specific terms, such description is for illustrative purposes only, and it is to be understood that changes and variations may be made without departing from the spirit or scope of the following claims.

What is claimed is:

1. An actuator device for moving an artificial leg of a person having a prosthesis for replacing an entire leg and hip joint including a trunk socket for positioning about the person's waist for receiving the trunk portion of the removed leg and an artificial leg connected to said trunk socket by a pivotable hip joint, said artificial leg comprising an artificial thigh section, an artificial lower leg section, and an artificial foot section, connected together by pivotable joints, said actuation device comprising:
 a. a first articulated hip joint assembly for positioning adjacent a natural leg of the person's body including:
  i. a housing;
  ii. flexible bladder means carried within said housing containing a fluid,
  iii. compressing means carried within said housing adapted for connection to said natural leg for compressing said bladder means in response to the walking movement of said natural leg,
 b. a second articulated hip joint assembly carried by said trunk socket of said prosthesis including:
  i. a housing,
  ii. flexible bladder means carried within said housing containing a fluid,
  iii. bladder engaging means carried within said housing connected to said artificial leg for moving said artificial leg in response to said bladder means being expanded, c. conduit means interconnecting said bladder means of said first and second hip joint assemblies;

whereby movement of said natural leg causes said compressing means to compress the bladder means and fluid therein of said first hip joint assembly forcing said fluid through said conduit means into said bladder means of said second hip joint assembly to expand said bladder means to engage and move said bladder engaging means causing said artificial leg connected thereto to move in a walking motion.

2. The device of claim 1 wherein said compressing means includes:
a. a fixed lobe member carried by said housing;
b. a rotatable shaft adapted for connection to said natural leg carried within said housing; and
c. a movable lobe carried on said shaft for rotation therewith;

whereby movement of natural leg rotates said movable lobe to compress said bladder means and said fluid contained therein.

3. The device of claim 2 wherein said bladder means is carried between said fixed lobe member and said movable lobe member.

4. The device of claim 1 wherein said bladder engaging means includes:
a rotatable shaft connected to said artificial leg carried in said housing of said second hip joint assembly;
a movable lobe member carried on said rotatable shaft for rotation therewith;
whereby said bladder means receiving said compressed fluid expands to engage said movable lobe member causing said artificial leg connected thereto to move in a walking motion.

5. The device of claim 4 wherein said bladder engaging means of said second articulated hip joint assembly further includes a fixed lobe member carried in said housing, said bladder means carried between said fixed and movable lobe members.

6. The device of claim 2 further comprising a linkage arm carried by one end of said rotatable shaft of said first articulated hip joint assembly, and a belt member adapted to connect said linkage arm to said natural leg so to cause said linkage arm to pivot with said leg causing said shaft to rotate reciprocally.

7. The device of claim 5 wherein said housings of said first and second hip joint assemblies are circular and said fixed and movable lobe members of each said assembly include opposed, quarter-circular lobes each having concave cut-out surfaces spaced on opposing sides of said shaft between which said flexible bladder means are carried.

8. The device of claim 7 wherein said bladder means of each of said first and second hip joint assemblies includes first and second flexible bladders spaced between said concave surfaces of said opposed lobes on opposing sides of said shaft.

9. The device of claim 8 further comprising control valve means connected in said conduit means for selectively delivering said fluid from either of said first and second bladders of said first hip joint assembly to either of said first and second bladders of said second hip joint assembly.

10. The device of claim 9 wherein said control valve means has an out of phase mode for delivering said compressed fluid from said first bladder of said first hip joint assembly to said second bladder of said second hip joint assembly and an inphase mode for delivering said fluid from said first bladder of said first hip joint assembly to said first bladder of said second hip joint assembly.

11. The device of claim 10 wherein movement of said natural leg forward during said inphase modes, rotates said shaft and movable lobe of said first assembly counter-clockwise compressing said first bladder therein forcing the fluid through said conduit means into said second bladder of said second assembly expanding said second bladder to rotate said movable lobe of said second assembly and thus said artificial leg counter-clockwise; said movable lobe of said second assembly rotating counter-clockwise simultaneously commmpressing fluid in said first bladder of said second assembly; said compressed fluid being delivered through said conduit means into said second bladder of said first assembly to further urge said movable lobe of said first assembly counter-clockwise.

12. An actuator device for moving an artificial leg of a person having a prosthesis for replacing an entire leg and hip joint including a trunk socket for positioning about the person's waist for receiving the trunk portion of the removed leg and an artificial leg connected to said trunk socket by a pivotable hip joint, said artificial leg comprising an artificial thigh section, an artificial lower leg section, and an artificial foot section connected together by pivotable joints, said actuation device comprising:
a. a first articulated hip joint assembly for positioning adjacent a natural leg of the person's body including:
i. a housing,
ii. a fixed lobe member,
iii. a rotatable shaft carried within said housing,
iv. a movable lobe member carried on said shaft for rotation therewith, and,
v. flexible bladder means carried within said housing between said fixed and movable lobe members containing a fluid,
b. a second articulated hip joint assembly carried by said trunk socket of the prosthesis including:
i. a housing,
ii. a fixed lobe member,
iii. a rotatable shaft member carried within said housing,
iv. a movable lobe member carried on said shaft for rotation therewith,
v. flexible bladder means carried within said housing between said fixed and movable lobe members containing a fluid,
c. conduit means interconnecting bladder means of said first and second hip joint assemblies;
d. means adapted for connecting said rotatable shaft of said first hip joint assembly to said natural leg, and means connecting said rotatable shaft of said second hip joint assembly to said artificial leg for moving said leg about the pivotable artificial hip joint,
whereby movement of said natural leg is adapted to rotate said shaft and movable lobe of said first hip joint assembly and cause compressing of said fluid in said bladder means therein and forcing of said fluid through said conduit means into said bladder means carried within said second hip joint assembly and expanding of said bladder means therein to engage said movable lobe member carried on said rotatable shaft within said second hip joint so as to move said entire artificial leg connected to said rotatable shaft in a walking motion.

* * * * *